United States Patent [19]

Drake et al.

[11] 4,230,857
[45] Oct. 28, 1980

[54] CARBONATES AND URETHANES OF 2,2'-ALKYLENE OR -CYCLOALKYLENE-BIS-4,6-DISUB-STITUTED PHENOLS AS STABILIZERS FOR ORGANIC MATERIALS

[75] Inventors: William O. Drake, Raritan, N.J.; Hans Hinsken, Lörrach, Fed. Rep. of Germany; Horst Mayerhoefer, Oberwil; Wolfgang H. Mueller, Allschwil, both of Switzerland

[73] Assignee: Sandoz Ltd., Basel, Switzerland

[21] Appl. No.: 908,721

[22] Filed: May 23, 1978

[30] Foreign Application Priority Data

May 23, 1977 [CH] Switzerland .......................... 6324/77
May 25, 1977 [CH] Switzerland .......................... 6439/77

[51] Int. Cl.² .................. C07D 295/20; C07C 125/06; C07C 69/96; C07D 321/12
[52] U.S. Cl. ................. 544/388; 260/45.8 N; 260/45.85 N; 260/45.85 P; 260/340.2; 260/463; 560/17; 560/25; 560/133
[58] Field of Search ......................................... 544/388

[56] References Cited

U.S. PATENT DOCUMENTS 3,632,631  1/1972  Wright et al. .......................... 71/100

FOREIGN PATENT DOCUMENTS 1453916  10/1976  United Kingdom .

*Primary Examiner*—Mark L. Berch
*Attorney, Agent, or Firm*—Gerald D. Sharkin; Richard E. Vila; Joseph J. Borovian

[57] ABSTRACT

Carbonates and urethanes of 2,2'-alkylene or -cycloalkylene-bis-4,6-disubstituted phenols are useful for stabilizing organic materials against the degradative effects of oxygen.

5 Claims, No Drawings

CARBONATES AND URETHANES OF 2,2'-ALKYLENE OR -CYCLOALKYLENE-BIS-4,6-DISUBSTITUTED PHENOLS AS STABILIZERS FOR ORGANIC MATERIALS

The present invention relates to carbonates and urethanes of 2,2'-alkylene or -cycloalkylene-bis-4,6-disubstituted phenols and their use for the stabilization of organic materials against the degradative effects of oxygen.

More particularly, the present invention provides compounds of formula I,

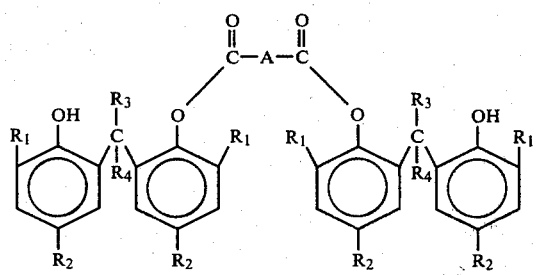

in which each $R_1$, independently, is $(C_{1-8})$alkyl, $(C_{5-9})$cycloalkyl or monomethyl$(C_{5-9})$cycloalkyl, each $R_2$, independently, is $(C_{1-8})$alkyl, $(C_{5-9})$cycloalkyl, halogen, phenyl or mono$(C_{1-9})$alkyl-phenyl, either each $R_3$, independently, is hydrogen, $(C_{1-18})$ alkyl, $(C_{5-9})$cycloalkyl or phenyl, and each $R_4$, independently, is hydrogen or $(C_{1-18})$alkyl, or one $$\diagdown_{CR_3R_4}\diagup$$

unit forms a $(C_{5-7})$ saturated aliphatic hydrocarbon ring, and each of $R_3$ and $R_4$ on the other $$\diagdown_{CR_3R_4}\diagup$$

unit are as defined above, or the other $$\diagdown_{CR_3R_4}\diagup$$

unit, independent from the first-mentioned $$\diagdown_{CR_3R_4}\diagup$$

unit, also forms a $(C_{5-7})$ saturated aliphatic hydrocarbon ring, and

A is a divalent organic group containing 2 to 70 carbon atoms and being attached to each adjacent carbonyl group by an oxygen atom or by a nitrogen atom.

In the above definition of formula I, it is preferred that both groups of formula

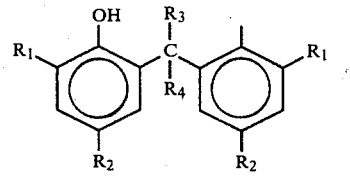

are identical. Further, within such groups, the $R_1$'s are preferably identical and the $R_2$'s are preferably identical.

When any $R_1$ is alkyl, this is preferably tertiary $(C_{4-8})$alkyl, more preferably tertiary butyl. The monomethyl-$(C_{5-9})$cycloalkyl radical signified by $R_1$ is preferably 1-methylcyclohexyl. Of all the significances of $R_1$, alkyl and 1-methylcyclohexyl are preferred, especially tertiary $(C_{4-8})$alkyl and 1-methylcyclohexyl, and alkyl is most preferred, especially $(C_{4-8})$alkyl.

When any $R_2$ is halogen, this means fluorine, chlorine or bromine. Preferably halogen is chlorine or bromine, more preferably chlorine. When any $R_2$ is alkyl, this is preferably methyl, ethyl or isopropyl, more preferably methyl or ethyl, and most preferably methyl. Of all the significances of $R_2$, alkyl is the most preferred, especially $R_2'$, as hereinafter defined.

When any $R_3$ or $R_4$ is alkyl, this is preferably methyl. Of all the significances, $R_3$ and $R_4$ are each preferably hydrogen or alkyl, especially $R_3'$ and $R_4'$, respectively, as hereinafter described.

The exact nature of A is not critical. The preferred significances of A, however, are A', i.e. the divalent groups of formulae (a) to (k):

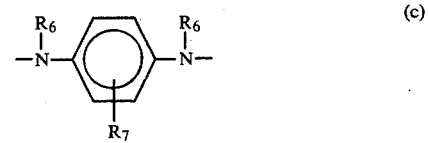

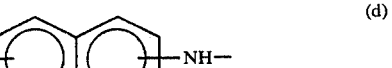

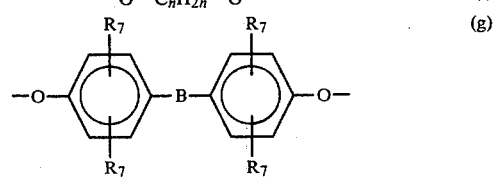

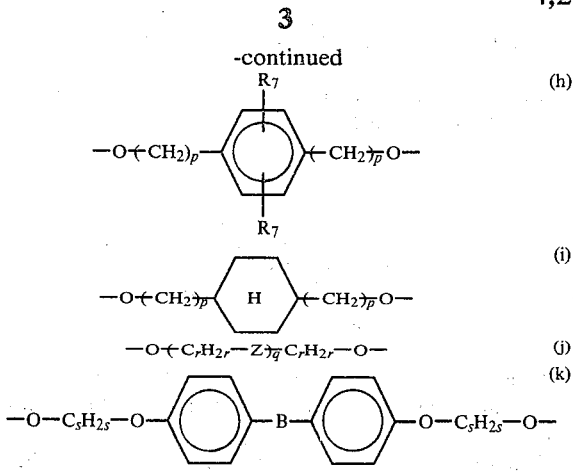

wherein each
- $R_5$, independently, is $(C_{1-18})$alkyl,
- n is an integer 2 to 12, each
- $R_6$, independently, is hydrogen or $(C_{1-4})$alkyl,
- $R_7$, or each $R_7$, independently, is hydrogen or $(C_{1-4})$alkyl,
- X is $-O-$, $-S-$, $-SO_2-$ or $-CR_8R_9-$,
- B is a direct bond, $-O-$, $-S-$, $-SO_2-$ or $-CR_8R_9-$, each
- p, independently, is 0 or an integer 1 to 4,
- q is an integer 1 to 6, each
- r, independently, is an integer 2 to 10, the or each Z, independently, is $-O-$, $-S-$ or $-SO_2-$, each
- s, independently, is an integer 2 to 6,
- $R_8$ is hydrogen, $(C_{1-18})$alkyl, $(C_{5-7})$cycloalkyl or phenyl, and
- $R_9$ is hydrogen or $(C_{1-18})$alkyl, with the proviso that the aggregate of the carbon atoms in $R_8$ and $R_9$ does not exceed 18.

Each $R_5$, independently, is preferably $(C_{1-5})$alkyl, more preferably methyl or ethyl, and most preferably methyl. Preferably both $R_5$'s are identical.

n is preferably an integer 2 to 10, more preferably 2, 3, 4 or 6, most preferably 2, 3 or 4.

When any $R_6$ is alkyl, this is preferably methyl. Each $R_6$, independently, is preferably alkyl. Preferably both $R_6$'s are identical.

When any $R_7$ is alkyl, this is preferably methyl. $R_7$, or each $R_7$, independently, is preferably hydrogen.

X is preferably oxygen or sulphur, more preferably oxygen.

B is preferably $-CR_8R_9-$.

In the group of formula (h), each p, independently, is preferably 0, 1 or 2, more preferably 0 or 1. Preferably both p's are identical.

In the group of formula (i), each p is preferably 1.

q is preferably an integer 1 to 4, more preferably 1.

Each r, independently, is preferably 2, 3 or 4, more preferably 2. Preferably both of all r's are identical.

Each Z, independently, is preferably $-O-$ or $-S-$. Preferably, when there are two or more Z's, these are identical.

Each s, independently, is preferably 2, 3 or 4, more preferably 2 or 3, and most preferably 2. Preferably both s's are identical.

When $R_8$ or $R_9$ is alkyl, this is preferably methyl, ethyl or propyl, more preferably methyl. $R_8$ is preferably hydrogen or alkyl, more preferably alkyl. $R_9$ is preferably alkyl.

In general, the group of formula (j) preferably contains no more than 50 carbon atoms.

Of the groups of formula (a) to (e), those of formulae (a) and (b) are preferred, and of those of formulae (f) to (k), those of formulae (g), (h), (i) and (j) are preferred, those of formulae (h), (i) and (j) are more preferred, and those of formulae (h) and (i) are most preferred. Of all the divalent groups signified by A', those of formulae (a) to (e) are generally preferred.

One particular class of compounds of formula I is constituted by the compounds in which $R_1$ is $(C_{1-8})$alkyl or $(C_{5-9})$cycloalkyl, and A is $A_x$, $A_x$ being a divalent group of one of the formulae (a) to (d), as defined above, and (e), as given above, in which X is $-O-$, $-S-$ or $-SO_2-$.

Another particular class of compounds of formula I is constituted by the compounds in which $R_1$ is $(C_{1-8})$alkyl or $(C_{5-9})$cycloalkyl, and A is $A_y$, $A_y$ being a divalent group of one of the formulae (f), (g), (j) and (k), as defined above, (h), as given above, in which each $R_7$ is hydrogen and each p is an integer 1 to 4, and (i), as given above, in which each p is an integer 1 to 4.

Further particular classes of compounds of formula I are those in which (i) A is a group of formula (a), (ii) A is a group of formula (b), (c) or (d), (iii) A is a group of formula (b), (c), (d) or (e), (iv) A is a group of formula (f), (v) A is a group of formula (g), (h) or (i), (vi) A is a group of formula (j), and (vii) A is a group of formula (k).

A preferred class of compounds of formula I is constituted by the compounds of formula Ia,

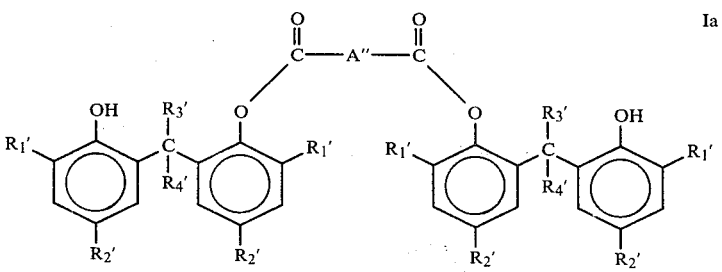

in which each
- $R_1'$, independently, is tertiary $(C_{4-8})$alkyl or 1-methylcyclohexyl, each
- $R_2'$, independently, is methyl, ethyl or isopropyl, each
- $R_3'$, independently, is hydrogen or methyl, each
- $R_4'$, independently, is hydrogen or methyl, and
- A'' is a divalent group of formula (a), (b), (g), (h), (i) or (j), as defined above.

In the above definition of formula Ia, it is preferred that both groups of formula

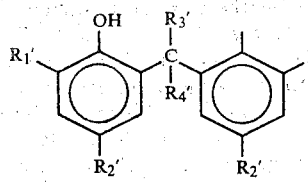

are identical. Also, it is preferred that within such groups, the $R_1$"s are identical and the $R_2$"s are identical.

The present invention further provides a process (a) for the production of those compounds of formula I in which A is attached to the adjacent carbonyl groups by nitrogen atoms, comprising reacting a compound or mixture of compounds of formula II,

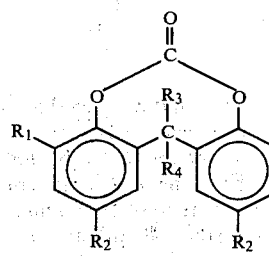

in which $R_1$, $R_2$, $R_3$ and $R_4$ are as defined above, with a compound of formula III, $$H-A_1-H \qquad III$$

in which $A_1$ is a divalent organic group containing 2 to 70 carbon atoms and being attached to the indicated hydrogen atoms by nitrogen atoms, preferably in a molar ratio compound(s) of formula II: compound of formula II of 2:1, respectively, and (b) for the production of those compounds of formula I in which A is attached to the adjacent carbonyl groups by oxygen atoms, comprising reacting a compound or mixture of compounds of formula IV,

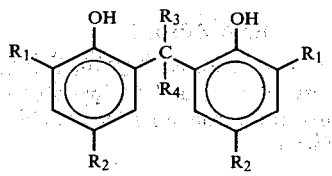

in which $R_1$, $R_2$, $R_3$ and $R_4$ are as defined above, with a compound of formula V,

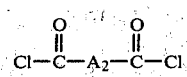

in which $A_2$ is a divalent organic group containing 2 to 70 carbon atoms and being attached to the indicated

groups of oxygen atoms,
preferably in a molar ratio compound(s) of formula IV: compound of formula V of 2:1, respectively.

The intermediate of formulae II, III, IV and V are either known or can be produced in analogous manner to the known compounds from available starting materials.

The conditions for reacting the compounds of formulae II and III are not critical. Preferably the mixed reagents are heated under an inert atmosphere at 120° to 200° C., more preferably at 150° to 170° C. The reaction may be carried out in the presence of an inert solvent, which preferably has a boiling point of at least 120° C., although the presence of a solvent is not essential.

In the case of the reaction between the compounds of formulae IV and V, the conditions are generally known for the type of reaction involved. Suitably the reaction is conducted at elevated temperature, and, to effect the removal of hydrogen chloride, a hydrogen chloride acceptor is preferably present.

The present invention further provides a method of stabilizing an organic material susceptible to the degradative effects of oxygen against such effects comprising treating said meterial with a stabilizing-effective amount of one or more compounds of formula I, as defined above. By the term "treating", as used herein, is meant either incorporating into the body of the organic material, or surface coating the organic material, e.g. in a manner known per se.

Suitable organic materials which are stabilized by the method of the present invention include such plastics materials as polyolefins, e.g. polyethylene and polypropylene, polystyrene, polyesters, polymethyl methacrylates, polyphenylene oxide, polyurethanes, polyamides, e.g. nylon, polypropylene oxides, polyacrylonitrile, copolymers of the aforementioned polymers, acrylonitrile-butadiene-styrene (ABS) terpolymers, and acrylic ester-styrene-acrylonitrile terpolymers, and such natural materials as natural rubber. The compounds of the present invention are especially suitable for stabilizing polyethylene, polypropylene, polyesters, polyurethanes, polyamides, polyacrylonitrile, copolymers of styrene and acrylonitrile and of styrene and butadiene, and terpolymers of acrylonitrile, butadiene and styrene and of acrylic ester, styrene and acrylonitrile, more particularly polyethylene, polypropylene, polyacrylonitrile and (ABS) terpolymers, even more particularly polyethylene, polypropylene and polyacrylonitrile, and most particularly polyethylene and polypropylene.

According to an embodiment of the method of the present invention, the compound(s) of formula I is(are) intimately mixed with a plastics material, e.g. polypropylene, preferably in particulate (granulate) form and preferably in a kneader or other suitable mixing device, to obtain even distribution of the compound(s) in the substrate. The treated material may then be forced into final shape, e.g. by extrusion to form, e.g. films, tubings or fibres.

The polymeric organic materials need not necessarily be in the final polymerized or condensed form before being treated with the compounds of the present invention. Thus, according to a second embodiment of the method of the present invention, particularly suited to the stabilization of polymeric or copolymeric materials, the compound(s) of formula I is (are) mixed with the appropriate monomer(s) or prepolymer(s) and/or pre-condensate(s) before polymerization or condensation is effected.

The suitable amount of stabilizing compound(s) of formula I employed in the method of the present invention will naturally depend on several factors, e.g. the mode of application, the particular compound(s) employed and the nature of the organic material to be treated. However, when the compound(s) is(are) incorporated into the body of the organic material, satisfactory results are generally obtained when the amount of compound(s) employed is in the range 0.01 to 5% of the weight of the organic material to be treated. Preferably, however, the amount is in the range 0.05 to 1%.

The organic materials may also be treated with other additives besides the compounds of formula I to improve their properties, e.g. other stabilizers or costabilizers against the degradative effects of oxygen, optionally possessing stabilizing properties against heat and/or light. Particularly preferred additives are distearyl thiodipropionate and tetrakis (methylene-3-dodecylthiopropionate)methane. The relative proportion by weight of the compound(s) of formula I to such additive(s) in the method of the present invention is preferably in the range 1:5 to 5:1, more preferably 1:4 to 1:1, e.g. 1:3, respectively.

The present invention further provides an organic material whenever treated according to the method of the present invention, as well any suitable composition containing one or more compounds of formula I, as defined above, for use in the method of the present invention. Such compositions, which may be referred to as master batches, generally comprise 50 to 90% by weight of the compound(s) of formula I, and a part of the substrate to be treated by the method of the present invention. The use of such a master batch in the method avoids the necessity for those practicing the method to initially make up the composition according to recommended ratio specifications before addition to the substrate to be stabilized. The master batch composition is readily worked into or applied onto the main body of the substrate by virtue of the presence of the same substrate in the master batch composition.

In the following Examples, which illustrate the present invention, parts and temperatures are by weight and in degrees Centigrade, respectively.

EXAMPLE 1

(a) Into a solution of 68 parts of 2,2'-methylene-bis-(4-methyl-6-tert-butyl-phenol) and 44 parts of triethylamine in 575 parts of toluene at a temperature within the range −15° to −10° are introduced 19.8 parts of phosgene over a period of 30 minutes. The cooling source is then removed and the mixture is stirred for 2 hours, after which the temperature is raised to 70° and stirring is continued for a further 4 hours at that temperature in a nitrogen stream for removal of excess phosgene.

The resulting precipitated triethylamine hydrochloride is removed by filtration and the filtrate is concentrated. The resulting solid is washed with methanol, resulting in a 75% yield of the compound of formula

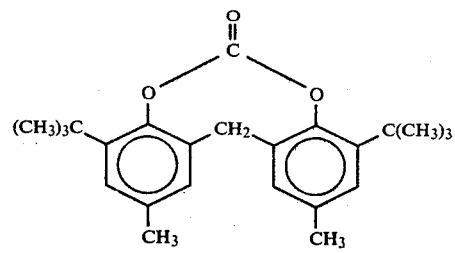

, m.p. 201°–202°.

(b) 7.3 Parts of the compound produced as described in (a) are mixed with 0.86 part of piperazine under a nitrogen atmosphere, and the mixture is heated to 180°. The mixture is observed to have a pasty consistency and, at 170°, after a heating time of 50 minutes, is in the molten state. After a further 40 minutes at constant temperature the melt assumes a pasty consistency. After cooling, the solidified product is ground in a mortar and stirred into a benzene fraction with a m.p. 140°–190°. White crystals are collected by filtration and consist of the compound of formula

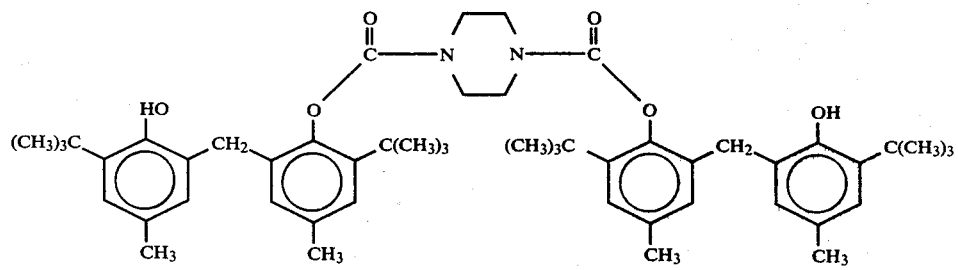

m.p. 258°–260°.

EXAMPLE 2

(a) To a mixture of 17 parts of 2,2'-methylene-bis-(4-methyl-6-tert-butyl-phenol) and 5.1 parts of triethylamine in 250 parts of toluene are added 8.8 parts of the compound of formula

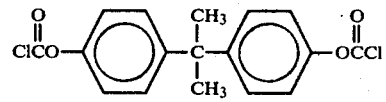

dissolved in 45 parts of toluene at room temperature, the addition being effected portionwise with stirring and under a nitrogen atmosphere. After 1 hour the triethylamine hydrochloride produced is removed by filtration and the filtrate is concentrated. The solid residue is crystallized from an isopropanol/water mixture. Produced is a compound of formula

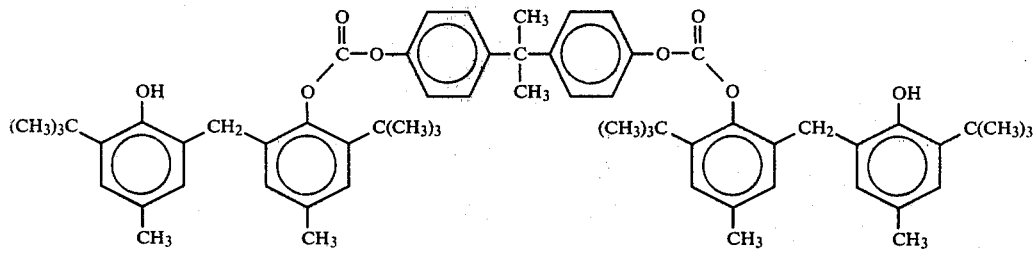

(2a)

m.p. 120°.

(b) In a manner analogous to that described in (a) the compound of formula

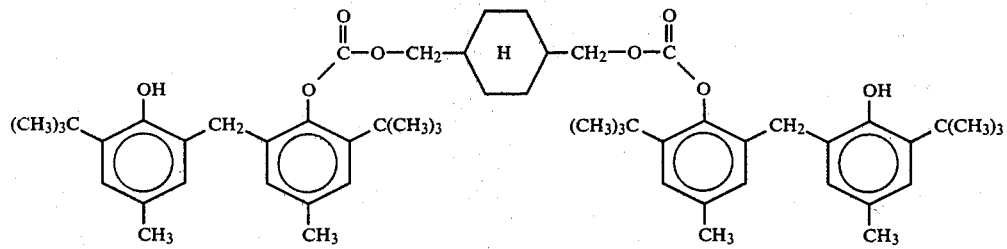

m.p. 100°, is produced.

EXAMPLES 3-12

In a similar manner to that described in Examples 1 and 2, the following compounds of formula I are produced from the appropriate starting materials.

a laboratory rolling mill (Schwabenthan) at 170° for 5 minutes. From the resulting rolled sheet are produced 0.5 mm thick sample plates using a press (Bucher Guyer) at 230° under a pressure of 2 tons for 2 minutes and 30 tons for 3 minutes. The test plates are then submitted to an accelerated ageing test in an oven at 150°. The time to the complete disintegration of the polymer, recognizable by the grainy clouding of the test samples and a complete loss of mechanical stability, is 1420

| Example | each $R_1$ | each $R_2$ | each $R_3$ | each $R_4$ | A |
|---|---|---|---|---|---|
| 3 | tert.-$C_4H_9$ | $CH_3$ | H | H | —N(CH₃)—CH₂CH₂—N(CH₃)— |
| 4 | tert.-$C_4H_9$ | tert.-$C_4H_9$ | H | H | —NH—⟨phenyl⟩—NH— |
| 5 | tert.-$C_4H_9$ | $CH_3$ | H | $CH_3$ | —NH—⟨naphthyl⟩—NH— |
| 6 | tert.-$C_4C_9$ | Cl | H | H | —NH—⟨phenyl⟩—O—⟨phenyl⟩—NH— |
| 7 | ⟨cyclohexyl-CH₃⟩ | $CH(CH_3)_2$ | H | H | —O$(CH_2)_3$O— |
| 8 | tert.-$C_4H_9$ | $C_2H_5$ | $CH_3$ | $CH_3$ | —O—⟨phenyl⟩—C(CH₃)₂—⟨phenyl⟩—O— |
| 9 | tert.-$C_4H_9$ | $CH_3$ | $CH_3$ | H | —O—CH₂—⟨phenyl⟩—CH₂—O— |
| 10 | neo-$C_5H_{11}$ | Cl | $CH_3$ | $CH_3$ | —O—CH₂CH₂—O—CH₂CH₂O— |
| 11 | tert.-$C_4H_9$ | $CH_3$ | $CH_3$ | H | —O—CH₂CH₂—S—CH₂CH₂—O— |
| 12 | ⟨cyclohexyl-CH₃⟩ | $CH(CH_3)_2$ | H | H | —O$(CH_2)_2$—O—⟨phenyl⟩—C(CH₃)₂—⟨phenyl⟩—O$(CH_2)_2$—O— |

APPLICATION EXAMPLE 99.6 Parts of unstabilized polypropylene (Profax 6501), 0.1 part of the compound produced as described in Example (1b), 0.2 part of distearylthiodipropionate and 0.1 part of calcium stearate are mixed together with hours. When the test is repeated using 2,2'-methylene-bis-(4-methyl-6-tert-butyl-phenol), i.e. the starting material used to produce the compound of formula (2a), instead of the compound produced as described in Example 1b), the corresponding time under the same conditions is 240 hours. The well known commercial product stearyl 4-hydroxy-3,5-ditert-butylphenyl-γ-propionate stabilizes under the same conditions up to 312 hours.

When the compound produced as described in Example (1b) is replaced by that of Example (2b) in the same test, a time of 1400 hours is achieved.

What is claimed is:

1. A compound of the formula,

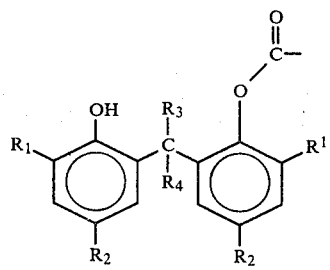

wherein each
  R₁, independently, is (C₁₋₈)alkyl, (C₅₋₉)cycloalkyl or monomethyl(C₅₋₉)cycloalkyl, each
  R₂, independently, is (C₁₋₈)alkyl, (C₅₋₉)cycloalkyl, halo, phenyl or mono (C₁₋₉)alkylphenyl, and either each
  R₃ is hydrogen, (C₁₋₁₈)alkyl, (C₅₋₉)-cycloalkyl or phenyl, and each
  R₄ is hydrogen or (C₁₋₁₈)alkyl, or each

unit forms a (C₅₋₇) saturated aliphatic hydrocarbon ring,
with the proviso that both groups of the formula

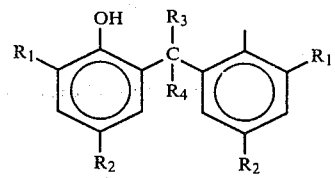

are identical.

2. A compound according to claim 1 of the formula,

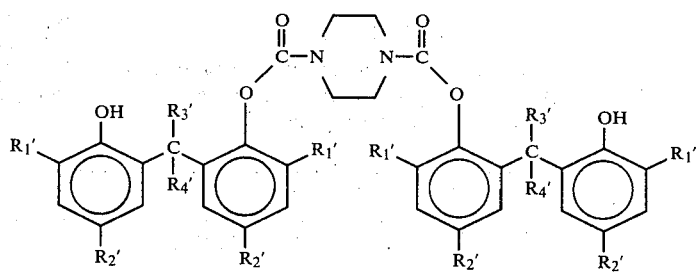

wherein each
  R₁', independently, is tertiary (C₄₋₈)-alkyl or 1-methylcyclohexyl, each
  R₂', independently, is methyl, ethyl or isopropyl, each
  R₃' is hydrogen or methyl, and each
  R₄' is hydrogen or methyl,
with the proviso that both groups of the formula

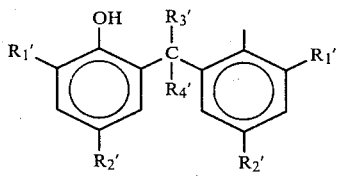

are identical.

3. A compound according to claim 1, in which all four R₁'s are identical, all four R₂'s are identical, both R₃'s are identical and both R₄'s are identical.

4. The compound according to claim 1 of the formula,

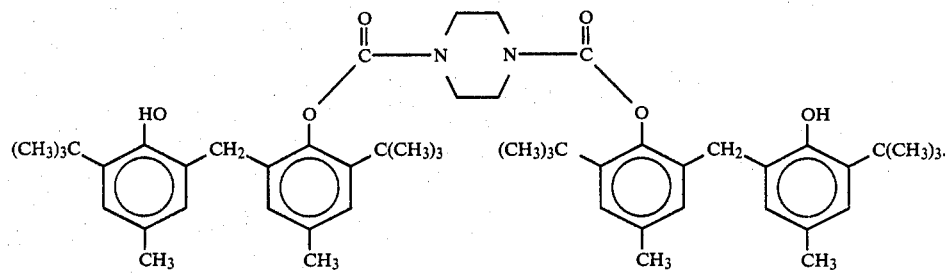
5. A compound according to claim 2, in which all four $R_1''$'s are identical, all four $R_2''$'s are identical, both $R_3''$'s are identical and both $R_4''$'s are identical.

UNITED STATES PATENT AND TRADEMARK OFFICE
CERTIFICATE OF CORRECTION

PATENT NO. : 4,230,857
DATED : October 28, 1980
INVENTOR(S) : William O. Drake/Hans Hinsken/Horst Mayerhoefer/ Wolfgang Mueller It is certified that error appears in the above—identified patent and that said Letters Patent is hereby corrected as shown below:

Column 6, the first line beneath the formula; delete the word "of" and insert in its place the word --by--.

Column 6, line 9; delete the word "intermediate" and insert in its place the word --intermediates--.

Column 6, line 62; delete the word "forced" and insert in its place the word --formed--.

Signed and Sealed this

Thirteenth Day of July 1982

[SEAL]

Attest:

Attesting Officer

GERALD J. MOSSINGHOFF
Commissioner of Patents and Trademarks